(12) United States Patent
Driver et al.

(10) Patent No.: US 7,538,256 B2
(45) Date of Patent: May 26, 2009

(54) REDUCTION OF ORGANIC HALIDES IN ALKYLATE GASOLINE

(75) Inventors: Michael S. Driver, San Francisco, CA (US); Gunther Dieckmann, Walnut Creek, CA (US)

(73) Assignee: Chevron U.S.A., Inc., San Ramon, CA (US)

( * ) Notice: Subject to any disclaimer, the term of this patent is extended or adjusted under 35 U.S.C. 154(b) by 378 days.

(21) Appl. No.: 11/609,739

(22) Filed: Dec. 12, 2006

(65) Prior Publication Data

US 2008/0142412 A1    Jun. 19, 2008

(51) Int. Cl.
*C07C 2/60* (2006.01)
*C07C 2/62* (2006.01)

(52) U.S. Cl. ............... 585/712; 585/725; 585/727; 585/728; 585/724

(58) Field of Classification Search ........... 585/712, 585/724, 725, 727, 728
See application file for complete search history.

(56) References Cited

U.S. PATENT DOCUMENTS 5,750,455 A * 5/1998 Chauvin et al. ............. 502/164

* cited by examiner

*Primary Examiner*—Thuan Dinh Dang
(74) *Attorney, Agent, or Firm*—Susan M. Abernathy; Steven H. Roth

(57) ABSTRACT

An alkylation process comprising contacting a first hydrocarbon feed comprising at least one olefin having from 2 to 6 carbon atoms and a second hydrocarbon feed comprising at least one isoparaffin having from 3 to 6 carbon atoms with a halide-based acidic ionic liquid catalyst under alkylation conditions to produce an alkylate containing an organic halide and contacting at least a portion of the alkylate with a hydrotreating catalyst in the presence of hydrogen under hydrotreating conditions to reduce the concentration of the organic halide is disclosed.

17 Claims, No Drawings

REDUCTION OF ORGANIC HALIDES IN ALKYLATE GASOLINE

FIELD OF THE INVENTION

The present invention relates to a process for the alkylation of light isoparaffins with olefins using a catalyst comprising an ionic liquid.

BACKGROUND OF THE INVENTION

In general, conversion of light paraffins and light olefins to more valuable cuts is very lucrative to the refining industries. This has been accomplished by alkylation of paraffins with olefins, and by polymerization of olefins. One of the most widely used processes in this field is the alkylation of isobutane with $C_3$ to $C_5$ olefins to make gasoline cuts with high octane number using sulfuric and hydrofluoric acids. This process has been used by refining industries since the 1940's. The process was driven by the increasing demand for high quality and clean burning high-octane gasoline.

Alkylate gasoline is a high quality and efficient burning gasoline that constitutes about 14% of the gasoline pool. Alkylate gasoline is typically produced by alkylating refineries isobutane with low-end olefins (mainly butenes). Currently, alkylates are produced by using HF and $H_2SO_4$ as catalysts. Although these catalysts have been successfully used to economically produce the best quality alkylates, the need for safer and environmentally friendlier catalysts systems has become an issue to the industries involved.

The quest for an alternative catalytic system to replace the current environmentally unfriendly catalysts has been the subject of varying research groups in both academic and industrial institutions. Unfortunately, thus far, no viable replacement to the current processes has been put into practice at commercial refineries.

Ionic liquids are liquids that are composed entirely of ions. The so-called "low temperature" Ionic liquids are generally organic salts with melting points under 100 degrees C., often even lower than room temperature. Ionic liquids may be suitable for example for use as a catalyst and as a solvent in alkylation and polymerization reactions as well as in dimerization, oligomerization acetylation, metatheses and copolymerization reactions.

One class of ionic liquids is fused salt compositions, which are molten at low temperature and are useful as catalysts, solvents and electrolytes. Such compositions are mixtures of components which are liquid at temperatures below the individual melting points of the components.

Ionic liquids can be defined as liquids whose make-up is entirely comprised of ions as a combination of cations and anions. The most common ionic liquids are those prepared from organic-based cations and inorganic or organic anions. The most common organic cations are ammonium cations, but phosphonium and sulphonium cations are also used. Ionic liquids of pyridinium and imidazolium are perhaps the most commonly used cations. Anions include; but not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many other. The most catalytically interesting ionic liquids for acid catalysis are those derived from ammonium halides and Lewis acids (such as $AlCl_3$, $TiCl_4$, $SuCl_4$, $FeCl_3$... etc). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts. The use of the fused salts of 1-alkylpyridinium chloride and aluminum trichloride as electrolytes is discussed in U.S. Pat. No. 4,122,245. Other patents which discuss the use of fused salts from aluminum trichloride and alkylimidazolium halides as electrolytes are U.S. Pat. Nos. 4,463,071 and 4,463,072.

U.S. Pat. No. 5,104,840 describes ionic liquids which comprise at least one alkylaluminum dihalide and at least one quaternary ammonium halide and/or at least one quaternary ammonium phosphonium halide; and their uses as solvents in catalytic reactions.

U.S. Pat. No. 6,096,680 describes liquid clathrate compositions useful as reusable aluminum catalysts in Friedel-Crafts reactions. In one embodiment, the liquid clathrate composition is formed from constituents comprising (i) at least one aluminum trihalide, (ii) at least one salt selected from alkali metal halide, alkaline earth metal halide, alkali metal pseudohalide, quaternary ammonium salt, quaternary phosphonium salt, or ternary sulfonium salt, or a mixture of any two or more of the foregoing, and (iii) at least one aromatic hydrocarbon compound.

Other examples of ionic liquids and their methods of preparation may also be found in U.S. Pat. Nos. 5,731,101; 6,797,853 and in U.S. Patent Application Publications 2004/0077914 and 2004/0133056.

In the last decade or so, the emergence of chloroaluminate ionic liquids sparked some interest in $AlCl_3$-catalyzed alkylation in ionic liquids as a possible alternative. For example, the alkylation of isobutane with butenes and ethylene in ionic liquids has been described in U.S. Pat. Nos. 5,750,455; 6,028,024; and 6,235,959 and open literature (*Journal of Molecular Catalysis*, 92 (1994), 155-165; "*Ionic Liquids in Synthesis*", P. Wasserscheid and T. Welton (eds.), Wiley-VCH Verlag, 2003, pp 275).

Aluminum chloride-catalyzed alkylation and polymerization reactions in ionic liquids may prove to be commercially viable processes for the refining industry for making a wide range of products. These products range from alkylate gasoline produced from alkylation of isobutane and isopentane with light olefins, to diesel fuel and lubricating oil produced by alkylation and polymerization reactions.

However, all the above processes using chloroaluminate ionic liquid catalyst produce trace amounts of organic chlorides in the hydrocarbon product during the reaction. Removal of the trace organic chlorides is desirable because organic chlorides are known to form dioxin during combustion. Removal of organic halides may also be desirable to meet product specifications. Analogous results will occur when ionic liquid catalysts based on halides other than chlorides are used.

SUMMARY OF THE INVENTION

The present invention relates to an alkylation process comprising contacting a first hydrocarbon feed comprising at least one olefin having from 2 to 6 carbon atoms and a second hydrocarbon feed comprising at least one isoparaffin having from 3 to 6 carbon atoms with a halide-based acidic ionic liqui, catalyst under alkylation conditions to produce an alkylate containing an organic halide and contacting at least a portion of the alkylate with a hydrotreating catalyst in the presence of hydrogen under hydrotreating conditions to reduce the concentration of the organic halide.

DETAILED DESCRIPTION

The present invention relates to an alkylation process comprising contacting a hydrocarbon mixture comprising at least one olefin having from 2 to 6 carbon atoms and at least one isoparaffin having from 3 to 6 carbon atoms with a halide-based acidic ionic liquid catalyst under alkylation conditions.

One component of a feedstock to the process of the present invention is at least one olefin having from 2 to 6 carbon atoms. This component may, for example, be any refinery hydrocarbon stream which contains olefins.

Another component of a feedstock to the process of the present invention is at least one isoparaffin having from 3 to 6 carbon atoms. This component may, for example, be any refinery hydrocarbon stream which contains isoparaffins.

The processes according to the present invention are not limited to any specific feedstocks and are generally applicable to the alkylation of $C_3$-$C_6$ isoparaffins with $C_2$-$C_6$ olefins from any source and in any combination.

In accordance with the present invention, a mixture of hydrocarbons as described above is contacted with a catalyst under alkylation conditions. A catalyst in accordance with the present invention comprises at least one acidic halide-based ionic liquid and may optionally include an alkyl halide promoter. The present process is being described and exemplified with reference certain specific ionic liquid catalysts, but such description is not intended to limit the scope of the invention. The processes described may be conducted using any acidic ionic liquid catalysts by those persons having ordinary skill based on the teachings, descriptions and examples included herein.

The specific examples used herein refer to alkylation processes using ionic liquid systems, which are amine-based cationic species mixed with aluminum chloride. In such systems, to obtain the appropriate acidity suitable for the alkylation chemistry, the ionic liquid catalyst is generally prepared to full acidity strength by mixing one molar part of the appropriate ammonium chloride with two molar parts of aluminum chloride. The catalyst exemplified for the alkylation process is a 1-alkyl-pyridinium chloroaluminate, such as 1-butyl-pyridinium heptachloroaluminate.

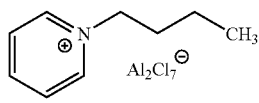

1-Butyl-pyridinium heptachloroaluminate

In general, a strongly acidic ionic liquid is necessary for paraffin alkylation, e.g. isoparaffin alkylation. In that case, aluminum chloride, which is a strong Lewis acid in a combination with a small concentration of a Broensted acid, is a preferred catalyst component in the ionic liquid catalyst scheme.

As noted above, the acidic ionic liquid may be any acidic ionic liquid. In one embodiment, the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

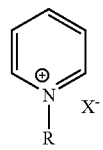

A

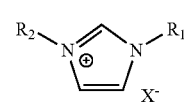

B

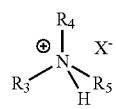

C

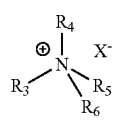

D where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same.

The acidic ionic liquid is preferably selected from the group consisting of 1-butyl-4-methyl-pyridinium chloroaluminate, 1-butyl-pyridinium chloroaluminate, 1-butyl-3-methyl-imidazolium chloroaluminate and 1-H-pyridinium chloroaluminate.

In a process according to the invention an alkyl halide may optionally be used as a promoter.

The alkyl halide acts to promote the alkylation by reacting with aluminum chloride to form the prerequisite cation ions in similar fashion to the Friedel-Crafts reactions. The alkyl halides that may be used include alkyl bromides, alkyl chlorides and alkyl iodides. Preferred are isopentyl halides, isobutyl halides, butyl halides, propyl halides and ethyl halides. Alkyl chloride versions of these alkyl halides are preferable when chloroaluminate ionic liquids are used as the catalyst systems. Other alkyl chlorides or halides having from 1 to 8 carbon atoms may be also used. The alkyl halides may be used alone or in combination.

A metal halide may be employed to modify the catalyst activity and selectivity. The metal halides most commonly used as inhibitors/modifiers in aluminum chloride-catalyzed olefin-isoparaffin alkylations include NaCl, LiCl, KCl, $BeCl_2$, $CaCl_2$, $BaCl_2$, $SrCl_2$, $MgCl_2$, $PbCl_2$, CuCl, $ZrCl_4$ and AgCl, as described by Roebuck and Evering (Ind. Eng. Chem. Prod. Res. Develop., Vol. 9, 77, 1970). Preferred metal halides are CuCl, AgCl, $PbCl_2$, LiCl, and $ZrCl_4$.

HCl or any Broensted acid may be employed as co-catalyst to enhance the activity of the catalyst by boasting the overall acidity of the ionic liquid-based catalyst. The use of such co-catalysts and ionic liquid catalysts that are useful in practicing the present invention is disclosed in U.S. Published Patent Application Nos. 2003/0060359 and 2004/0077914. Other co-catalysts that may be used to enhance the activity include IVB metal compounds preferably IVB metal halides such as $ZrCl_4$, $ZrBr_4$, $TiCl_4$, $TiCl_3$, $TiBr_4$, $TiBr_3$, $HfCl_4$, $HfBr_4$ as described by Hirschauer et al. in U.S. Pat. No. 6,028,024.

Due to the low solubility of hydrocarbons in ionic liquids, olefins-isoparaffins alkylation, like most reactions in ionic liquids is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range 1 to 100, for example, advantageously in the range 2 to 50, preferably in the range 2 to 20. In a semi-batch system the isoparaffin is introduced first then the olefin, or a mixture of isoparaffin and olefin. Catalyst volume in the reactor is in the range of 2 vol % to 70 vol %, preferably in the range of 5 vol % to 50 vol %. Vigorous stirring is desirable to ensure good contact between the reactants and the catalyst. The reaction temperature can be in the range −40° C. to +150° C., preferably in the range −20° C. to +100° C. The pressure can be in the range from atmospheric pressure to 8000 kPa, preferably sufficient to keep the reactants in the liquid phase. Residence time of reactants in the vessel is in the range a few seconds to hours, preferably 0.5 min to 60 min. The heat generated by the reaction can be eliminated using any of the means known to the skilled person. At the reactor outlet, the hydrocarbon phase is separated from the ionic phase by decanting, then the hydrocarbons are separated by distillation and the starting isoparaffin which has not been converted is recycled to the reactor.

Typical alkylation conditions may include a catalyst volume in the reactor of from 5 vol % to 50 vol %, a temperature of from −10° C. to +100° C., a pressure of from 300 kPa to 2500 kPa, an isopentane to olefin molar ratio of from 2 to 8 and a residence time of 5 min to 1 hour.

In one embodiment of a process according to the present invention, high quality gasoline blending components of low volatility are recovered from the alkylation zone. Those blending components are then preferably blended into gasoline.

As noted previously, alkylation using chloroaluminate ionic liquid catalyst produces trace amounts of organic chlorides in the hydrocarbon product during the reaction. Removal of the trace organic chlorides is desirable because organic chlorides are known to form dioxin during combustion. Removal may also be desirable to meet product specifications. Analogous results will occur when ionic liquid catalysts based on halides other than chlorides are used.

In accordance with the invention, the organic halide content of the product of the alkylation reaction can be reduced by hydrotreating the reaction product. The hydrotreating may also be done after the reaction product is mixed with other components, for example, to make gasoline, in which case the gasoline is hydrotreated.

In a preferred embodiment, the organic chloride concentration of alkylate which has been prepared using a chloroaluminate ionic liquid catalyst is reduced by contacting the alkylate with a hydrotreating catalyst in a hydrotreating zone in the presence of hydrogen under mild hydrotreating conditions, which include temperatures from 200° F. to 600° F. and hydrogen pressures of 1 to 300 psig. This has resulted in a reduction of chloride content of gasoline from about 400 ppm to less than 5 ppm. In addition, the gasoline that has been hydrotreated under these conditions is not degraded.

A process according to the present invention may use any hydrotreating catalyst. Preferred are solid catalyst systems that contain precious metals such as palladium and/or platinum on either activated carbon or a silica support.

The following Example is illustrative of the present invention, but is not intended to limit the invention in any way beyond what is contained in the claims which follow.

EXAMPLE

The product from the alkylation reaction of isobutane with butenes using N-butylpyridinium heptachloroaluminate catalyst was determined to have an alkyl chloride content of 422 ppm by X-Ray Fluorescence (XRF) Spectroscopy. To dechlorinate this product, a 4.5 gram sample of a hydrotreating catalyst consisting of Pd/Pt dispersed on a silica/alumina support diluted in 11 grams of silica carbide grit was loaded into a ⅜" diameter tube reactor and reduced under flowing $H_2$ at 5.3 cc/min at 200 psig and 250 F for 2 hours. The alkylate product was then passed downflow over the catalyst at a rate of 17 g/hr (LHSV=4 $hr^{-1}$) at 400 F with an $H_2$ flow of 35.6 cc/min and a pressure of 200 psig. A sample of the hydrotreated product was collected and determined to have an alkyl chloride content of 5.2 ppm by XRF spectroscopy.

There are numerous variations on the present invention which are possible in light of the teachings and supporting examples described herein. It is therefore understood that within the scope of the following claims, the invention may be practiced otherwise than as specifically described or exemplified herein.

What is claimed is:

1. An alkylation process comprising contacting a first hydrocarbon feed comprising at least one olefin having from 2 to 6 carbon atoms and a second hydrocarbon feed comprising at least one isoparaffin having from 3 to 6 carbon atoms with a halide-based acidic ionic liquid catalyst under alkylation conditions to produce an alkylate containing an organic halide and contacting at least a portion of the alkylate with a hydrotreating catalyst in the presence of hydrogen under hydrotreating conditions to reduce the concentration of the organic halide in the alkylate; where the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

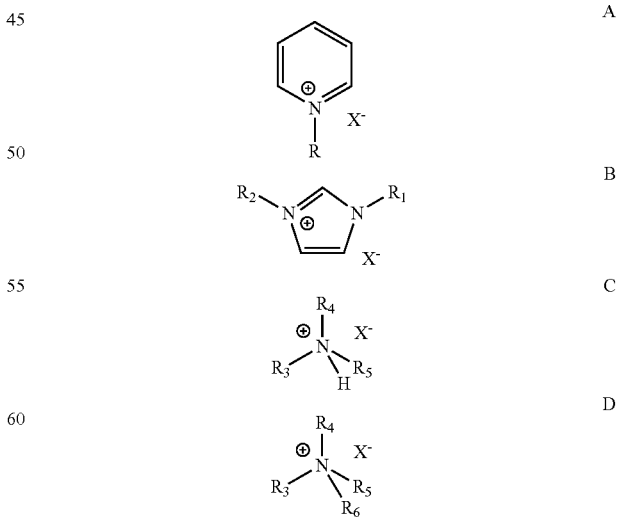

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same; and wherein the ionic liquid catalyst further comprises an alkyl halide.

2. The process according to claim 1, wherein the acidic ionic liquid is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

3. The process according to claim 1, wherein the hydrogenation conditions include temperatures from 200° F. to 600° F. and hydrogen pressures from 1 to 300 psig.

4. The process according to claim 1, wherein the isoparaffin is selected from the group consisting of isobutane, isopentanes and mixtures thereof.

5. The process according to claim 1, wherein the olefin is selected from the group consisting of ethylene, propylene, butylenes, pentenes and mixtures thereof.

6. The process according to claim 1, wherein the alkylation conditions include a catalyst volume in the reactor of from 5 vol % to 50 vol %, a temperature of from −10° C. to 100° C., a pressure of from 300 kPA to 2500 kPa, an isopentane to olefin molar ratio of from 2 to 8 and a residence time of 1 minute to 1 hour.

7. The process according to claim 1, further comprising recovering high quality gasoline blending components of low volatility.

8. The process according to claim 1, where the alkyl halide is selected from the group consisting of methyl halide, ethyl halide, propyl halide, 1-butyl halide, 2-butyl halide, tertiary butyl halide, pentyl halides, iospentyl halide, hexyl halides, isohexyl halides, heptyl halides, isoheptyl halides, octyl halides and isooctyl halides.

9. The process according to claim 1, wherein the hydrogenation catalyst comprises platinum, palladium or their mixtures on a solid support.

10. In an alkylation process in which at least one olefin having from 2 to 6 carbon atoms and at least one isoparaffin having from 3 to 6 carbon atoms are contacted in an alkylation zone under alkylation conditions with a catalyst comprising a chloride-based acidic ionic liquid to produce an alkylate, the improvement comprising reacting at least a portion of the alkylate with a hydrotreating catalyst in the presence of hydrogen under hydrotreating conditions to reduce the concentration of organic chlorides in the alkylate; where the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

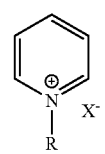

A

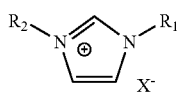

B

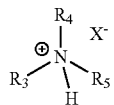

C

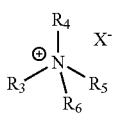

D where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same; and wherein the ionic liquid catalyst further comprises an alkyl halide.

11. The process according to claim 10, wherein the acidic ionic liquid is selected from the group consisting of 1-butyl-4-methyl-pyridinium chloroaluminate (BMP), 1-butyl-pyridinium chloroaluminate (BP), 1-butyl-3-methyl-imidazolium chloroaluminate BMIM) and 1-H-pyridinium chloroaluminate (HP).

12. The process according to claim 10, wherein the hydrotreating conditions include temperatures from 93° C. to 316° C. (200° F. to 600° F.) and hydrogen pressures from 1 to 300 psig; and wherein the hydrotreating catalyst comprises platinum, palladium or their mixtures on a solid support.

13. (The process according to claim 10, wherein the olefin is selected from the group consisting of ethylene, propylene, butylenes, pentenes and mixtures thereof.

14. The process according to claim 10, wherein the isoparaffin is selected from the group consisting of isobutane, isopentanes and mixtures thereof.

15. An alkylation process, comprising:
a. contacting a first hydrocarbon feed comprising at least one olefin having from 2 to 6 carbon atoms and a second hydrocarbon feed comprising at least one isoparaffin having from 3 to 6 carbon atoms with a halide-based acidic ionic liquid catalyst under alkylation conditions to produce an alkylate containing an organic halide;
b. adding the alkylate to other gasoline blending components to produce an alkylate gasoline; and
c. contacting at least a portion of the alkylate gasoline with a hydrotreating catalyst in the presence of hydrogen under hydrotreating conditions to reduce the concentration of the organic halide in the alkylate gasoline; where the acidic ionic liquid is a chloroaluminate ionic liquid prepared by mixing aluminum trichloride ($AlCl_3$) and a hydrocarbyl substituted pyridinium halide, a hydrocarbyl substituted imidazolium halide, trialkylammonium hydrohalide or tetraalkylammonium halide of the general formulas A, B, C and D, respectively,

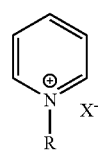

A

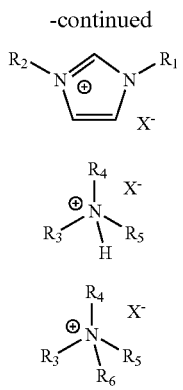

where R=H, methyl, ethyl, propyl, butyl, pentyl or hexyl group and X is a halide and preferably a chloride, and $R_1$ and $R_2$=H, methyl, ethyl, propyl, butyl, pentyl or hexyl group and where $R_1$ and $R_2$ may or may not be the same, and $R_3$, $R_4$, and $R_5$ and $R_6$=methyl, ethyl, propyl, butyl, pentyl or hexyl group and where $R_3$, $R_4$, $R_5$ and $R_6$ may or may not be the same; and wherein the ionic liquid catalyst further comprises an alkyl halide.

16. The process of claim 10 or claim 15, wherein the hydrotreating catalyst comprises platinum, palladium, or their mixtures, and is on a solid support.

17. The process of claim 1 or claim 10, wherein the alkylate is a gasoline blending component.

* * * * *